(12) United States Patent
Ewell

(10) Patent No.: US 11,932,002 B2
(45) Date of Patent: Mar. 19, 2024

(54) GARMENT MULTILAYERED-LINING SEWING PROCESS

(71) Applicant: EC BRAND COM IMP EXP DE VEST EM GERAL LTDA, Sorocaba (BR)

(72) Inventor: Emily Steed Ewell, Sorocaba (BR)

(73) Assignee: EC BRAND COM IMP EXP DE VEST EM GERAL LTDA, Sorocaba (BR)

(*) Notice: Subject to any disclaimer, the term of this patent is extended or adjusted under 35 U.S.C. 154(b) by 1057 days.

(21) Appl. No.: 16/479,815

(22) PCT Filed: Aug. 28, 2017

(86) PCT No.: PCT/BR2017/050249
§ 371 (c)(1),
(2) Date: Jul. 22, 2019

(87) PCT Pub. No.: WO2019/041005
PCT Pub. Date: Mar. 7, 2019

(65) Prior Publication Data
US 2021/0206144 A1    Jul. 8, 2021

(51) Int. Cl.
*D05B 93/00* (2006.01)
*A61F 13/15* (2006.01)
(Continued)

(52) U.S. Cl.
CPC .......... *B32B 7/09* (2019.01); *A61F 13/15723* (2013.01); *B32B 5/06* (2013.01);
(Continued)

(58) Field of Classification Search
CPC .......... D05B 93/00; D05B 93/02; D05B 1/26; B23B 7/09; B23B 2038/008; A61F 13/475; A61F 13/4963; A61F 13/15739
See application file for complete search history.

(56) References Cited

U.S. PATENT DOCUMENTS

| | | | |
|---|---|---|---|
| 4,573,987 A * | 3/1986 | Lamb, Jr. .......... | A61F 13/49004 D24/126 |
| 7,322,966 B1 * | 1/2008 | Deerin .................... | A61F 13/74 604/385.15 |

(Continued)

FOREIGN PATENT DOCUMENTS

| | | |
|---|---|---|
| CN | 201444957 U | 5/2010 |
| CN | 101906681 A | 12/2010 |

(Continued)

*Primary Examiner* — Danny Worrell
(74) *Attorney, Agent, or Firm* — Hamre, Schumann, Mueller & Larson, P.C.

(57) ABSTRACT

This disclosure relates to a sewing process of a breathable, reusable, and leak-proof garment multilayered-lining having absorbent, antimicrobial, waterproofing, and steam dispersion functions. Such lining aims at preventing body fluids such as sweat, blood, vaginal fluids, menstrual fluid, urine, breast milk, or post-surgical fluids from leaking. Such a lining provides the absorbent, antimicrobial, waterproofing, and steam dispersion functions. The lining may be sewed or adhered to the garment piece including: men's and women's underwear, shorts, short pants, skirts, pants, bras, shirts, T-shirts, jumpsuits, body shapers, dresses, men's and women's nightwear, etc. The sewing process creates channels for the liquid and creates a non-linear U-shaped structure on the lining to prevent leakage from the sides. The disclosed lining also has a reduced number of layers on its sides due to one of its layers being smaller in width than the other layers, making the coating thinner for the wearer.

19 Claims, 1 Drawing Sheet

(51) Int. Cl.
  *B32B 5/06* (2006.01)
  *B32B 7/09* (2019.01)
  *D06M 13/00* (2006.01)
  *B32B 38/00* (2006.01)

(52) U.S. Cl.
  CPC ............ *D05B 93/00* (2013.01); *D06M 13/00* (2013.01); *B32B 2038/008* (2013.01)

(56) References Cited

U.S. PATENT DOCUMENTS

| | | | | |
|---|---|---|---|---|
| 10,750,793 | B1* | 8/2020 | Theodoridis | A41B 9/001 |
| 11,154,431 | B1* | 10/2021 | Yip | A41B 17/00 |
| 11,357,269 | B2* | 6/2022 | Ewell | A41B 17/00 |
| 11,375,756 | B1* | 7/2022 | White | A41B 17/00 |
| 11,612,191 | B1* | 3/2023 | White | A41B 9/00 |
| | | | | 2/400 |
| 2014/0039432 | A1* | 2/2014 | Dunbar | A61F 13/66 |
| | | | | 604/394 |
| 2014/0378935 | A1* | 12/2014 | Arayama | A61F 13/494 |
| | | | | 604/385.101 |
| 2016/0184146 | A1* | 6/2016 | Tulk | A01N 37/06 |
| | | | | 604/385.15 |
| 2020/0170309 | A1* | 6/2020 | Ewell | B32B 27/12 |
| 2020/0383393 | A1* | 12/2020 | Caden | B32B 27/40 |
| 2021/0177676 | A1* | 6/2021 | Kajanthan | A41D 31/10 |
| 2021/0206144 | A1* | 7/2021 | Ewell | B32B 7/09 |
| 2023/0128088 | A1* | 4/2023 | Deshaies | A61F 13/496 |
| | | | | 2/272 |
| 2023/0129586 | A1* | 4/2023 | Greco | A41D 7/00 |
| | | | | 604/383 |
| 2023/0157376 | A1* | 5/2023 | Towns-Scott | A41D 27/20 |
| | | | | 2/406 |

FOREIGN PATENT DOCUMENTS

| | | |
|---|---|---|
| CN | 202396517 U | 8/2012 |
| CN | 103938361 A | 7/2014 |
| CN | 104862856 A | 8/2015 |
| CN | 105442325 A | 3/2016 |
| CN | 105803787 A | 7/2016 |
| CN | 106183210 A | 12/2016 |
| FR | 2247199 A1 | 5/1975 |
| JP | H04197353 A | 7/1992 |
| JP | H08182699 A | 7/1996 |
| JP | H10165432 A | 6/1998 |
| JP | 2011135998 A | 7/2011 |
| KR | 101688837 B1 | 12/2016 |

* cited by examiner

GARMENT MULTILAYERED-LINING SEWING PROCESS

CROSS-REFERENCE TO RELATED APPLICATIONS

This application is a national stage entry under 35 U.S.C. 371 of PCT Patent Application No. PCT/BR2017/050249, filed Aug. 28, 2017, the entire contents of which is incorporated herein by reference.

FIELD OF THE DISCLOSURE

This disclosure relates to a sewing process of a breathable, reusable, and leak proof garment multilayered lining having absorbent, antimicrobial, waterproofing, and steam dispersion functions.

BACKGROUND

Clothes with functionality provide solutions for customers and are able to contribute to well-being and health. Currently, there are many solutions to problems related to release of body fluids such as sweat, blood, vaginal fluids, menstrual fluids, urine, breast milk or post-surgical fluids.

However, many of these solutions for releasing body fluids do not reflect practical solutions, since they require daily application and reapplication. Moreover, disposal after use may implicate other technical problems for consumer.

Thus, washable and reusable products for solving problems of releasing body fluids are desirable by the costumer. In addition, high durability of such products is a desirable factor as well.

This disclosure relates to a sewing process of a breathable, reusable, and leak proof garment multilayered lining. Such lining mainly aims at preventing body fluids, such as sweat, blood, vaginal fluids, menstrual fluids, urine, breast milk or post-surgical fluids from leaking. The lining is sewed to the garment piece aiming at improving quality of life and well-being of costumers. Said garments in which the lining may be applied include: men and women underwear, shorts, short pants, skirts, pants, bras, shirts, T-shirts, jumpsuits, body shapers, dresses, men and women nightwear, and others.

Said multilayer lining for garment has at least four layers of which at least one has antimicrobial functionality that is the key to ensure health and well-being of wearer.

The fact of said lining is reusable ensures that disclosed embodiments provide an economical and hygienic solution for wearer, in addition to positively contribute to environment.

The breathability of the multilayer lining for garment is essential for wearer to keep the temperature stability and to ensure comfort during its use. Moreover, the lining has antimicrobial function with durability of up to 60 washes using washing machine. In order to preserve its antimicrobial characteristic after many washes, the lining must be cleaned without fabric softener or bleach so that it ensures its functions.

Such many layers comprising said lining in combination with sewing process of the disclosure are the key to the anti-leak function of the lining, since they solve the technical problem of waterproofing coatings used to be leaked over the sides when they are full.

The sewing process that is object of this invention channels the liquid and creates a non-linear U-shaped structure on the lining so that it prevents leak over the sides. The present lining also reduces the number of layers on the sewing stitches of its sides, since the absorbent layer is slightly smaller in width than the other layers, providing more comfortable edges and allowing for feeling of a thinner lining for wearer.

The U.S. patent application No. US 20140039432 discloses many embodiments of multilayer garment lining. A lining with a first layer having an absorption and draining function; a second antimicrobial layer; a third polyurethane waterproofing and breathable layer, and a fourth outer fabric layer of the garment is disclosed in one of its embodiment. While the Figures herein suggest the seam arrangement, it is not possible by the teachings herein to assess whether the layers are sequentially affixed by seams with tacking stitch (inner layer), glove stitch (inner layer with middle ones) and three-thread overedge stitch (inner layer with middle and outer ones).

BRIEF DESCRIPTION OF THE INVENTION

This disclosure relates to sewing process of a breathable, reusable, and leak proof garment multilayered lining. Such lining aims at preventing body fluids such as sweat, blood, vaginal fluids, menstrual fluid, urine, breast milk or post-surgical fluids from leaking. Such lining has absorbent, antimicrobial, waterproofing, and steam dispersion functions.

The sewing process that is object of this invention channels the liquid and creates a non-linear U-shaped structure on the lining so that it prevents leak over the sides. The present lining also has a reduced number of sewing stitches on its sides, since the absorbent layer is slightly smaller in width than the other layers, providing more comfortable edges and allowing for feeling of a thinner lining for wearer.

BRIEF DESCRIPTION OF THE DRAWINGS

Disclosed embodiments are further described with reference to the embodiments depicted in the drawings.

DETAILED DESCRIPTION OF THE INVENTION

This disclosure relates to a sewing process of a garment multilayered-lining that may be used in garment pieces, for example, for men's and women's underwear in general.

The multilayer lining of the disclosure resists up to 60 washes in washing machine—carefully treated, it is in compliance with ISO rule 20743, resists to waterproofing test for 12 h applying 500 ml of fluid, and is permeable to air.

Figure 1:
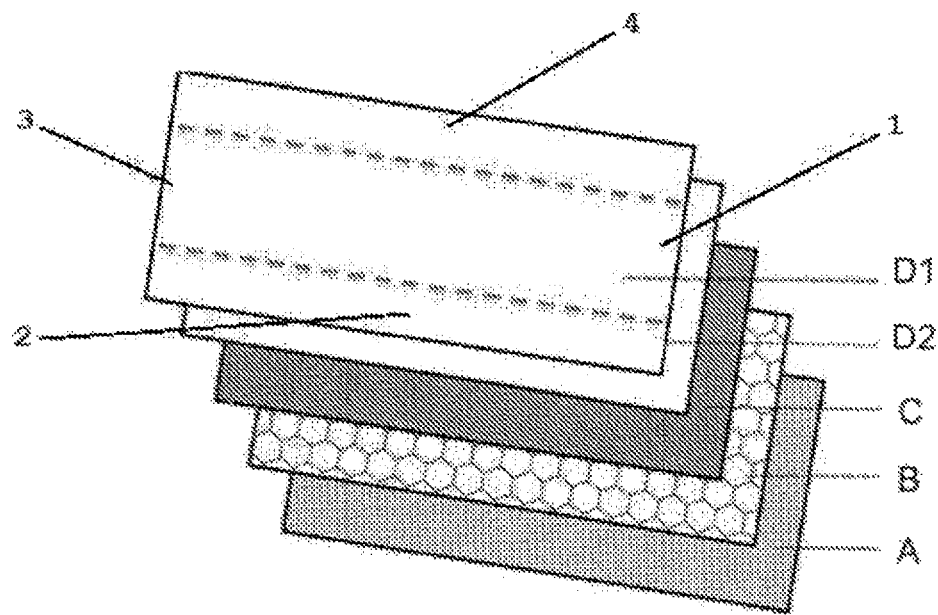
FIG. 1 is a schematic view showing a multilayer lining for garment composed by layers A, B, C, D1, and D2.

For sewing the lining, cutting layers A, B, C, D1, and D2 is needed. B, C, and D1 should be cut being the same size as the lining as well as the same size as one another. Layer A should be cut being the same width as the lining, as demonstrated by the width related to the forward and backward sides (3 and 1) in the FIG. 1, and the length related to the sides of the lining-legs opening (2 and 4) being in accordance with the garment design.

Layer D2 in turn should be at least 0.5 to 1.5 shorter in the length related to the sides of the lining-legs opening (2 and 4) than the length related to the sides of the lining-legs opening (2 and 4) of the layers B, C, and D1. With this change, the global volume of the lining is reduced on the edges, providing more comfort to wearer. Layer D2 is equal in width related to the forward and backward sides (3 and 1) of the garment piece to the layers B, C, and D1.

The sewing process is carried out by the following stages:

Stage 1: Sewing the layers D1 and D2 by using chain stitch (ISO 101), zig-zag lockstitch (ISO 304) or double back stitch (ISO 401) on sides 2 and 4, 1-3 cm from the edges D1;

Stage 2: Sewing the layers B, C, D2, and D1 on the sides 1 and 3;

wherein the layer A) may be sewed on other inner garment layer for aesthetical purposes by using blind stitch, three-thread overedge stitch (ISO 504), zig-zag lockstitch (ISO 304) or flatseams (ISO 607);

wherein the layer B) may be sewed by using an additional finishing stitch on the gusset, using three-thread overedge stitch (ISO 504), two-thread overedge stitch (ISO 503) or four thread mock safety (ISO 512);

Stage 3: Sewing the layers A, B, C, and D1 on the sides of the lining-legs opening with fabric tape or sewing using blind stitch, or three-thread overedge stitch (ISO 504), or zig-zag lockstitch (ISO 304), or bottom cover stitch (ISO 406). These layers may additionally be joined by sewing with accessories as elastics, laces or other finishings.

Figure 2:
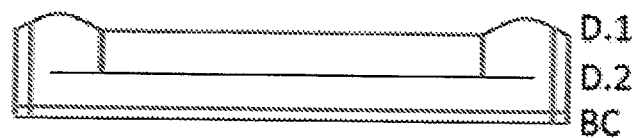
FIG. 2 shows the layers D1, D2, B, and C joined by a specific sewing process.

The constituent layers of the lining in combination with the sewing process of the disclosure are the key to the anti-leak function of the lining, since they solve the technical problem of waterproofing coatings used to be leaked over the sides when they are full. Once said lining is composed by fabric, and made in a planar shape on the gusset, the sewing process channels the liquid and creates a non-linear U-shaped structure on the lining so that it prevents leak over the sides. The present lining also has a reduced number of layers on its edges due to the layer D2 is shorter in length if compared to the other layers, making the coating more comfortable for wearer. FIG. 2 shows the lining of which layers D1, D2, B and C corresponding to the stage 2 of the sewing process.

All the seams should be made with needles of 60 to 90 in size aiming at producing small holes and reduce every single possibility of lining leak. All seams uses thread 120-160 of polyester or polyester thread that received antimicrobial and anti-leak treatment. The polyester reduces capillarity over lining seams to the piece side, the treated threads improve the general performance of the lining.

The multilayer lining includes 5 layers, a first layer A of outer finishing material, that may, for example, be selected from the group material comprising cotton, modal, bamboo, viscose, polyester, microfiber, nylon, including combinations with elastane, lycra, and spandex.

A second layer B of natural or synthetic material selected from the group comprising cotton, polyester, bamboo, viscose, tinsel, modal, and nylon, that is between 60 and 350 g/m2 by weight, and may have suitcase, woven fabric, fleece, terry cloth or microfiber structure. The second layer B is chemically treated with antimicrobial product, for example, with product containing silver ions, for example, Silpure (a Thomson Research associates product).

A third layer C is a 0.015 to 0.020 mm breathable thermoplastic polyurethane one that is applied using no harmful chemical products, as in the state of art.

The third layer C is affixed to the second layer B by lamination process by applying heat. The other layers are joined by a specific sewing process.

The combination of the waterproofing layer C and antimicrobial layer B promotes greater antimicrobial effectiveness due to this layer is in the lower part of the multilayer lining, such that the most of the absorbed liquid would not contact the antimicrobial fabric. In addition, such combination provides more flexibility to the functionality on the layers towards the body, in addition to the fact that the global volume of the multilayer linings is smaller resulting in more comfort to wearer.

A fourth layer D1, which is the inner layer of the lining, may be composed by 51% of modal, viscose, bamboo, carbon or cotton with 90 to 300 gsm. The layer D1 may be knitted or woven in a special standard to be created with: (1) greater aperture or channels for the liquid that facilitates the mechanical passage of the liquid by capillarity to the next layer, and that includes a more viscous and/or less polarized liquids than the water, and with a (2) 3D texture providing a greater superficial area in contact with the body—allowing for a faster drying and a drier touch than a single- or double-mesh Jersey fabric of comparable weight and denier.

A fifth layer D2, which is the absorbent layer, is composed by at least 90% of polyester or microfiber, Coolplus® fiber being embodied with rapid absorption technology, rapid drying, and cooling properties with 100 to 300 gsm. The coolplus fibers are distinct from the more commonly used technology to obtain rapid absorption and drying clothes, since such technologies use chemical products to obtain rapid absorption and drying functions, which are repelled from the fabric due to washings. It is important to mention the advantage of the disclosure related to the coolplus fibers which are embodied in the fabric and do not come off over time, assisting the temperature control on the lining. Depending on the purpose of the multilayer lining for garment, this layer may be in a greater amount on the lining.

Those skilled in the art will value the knowledge herein presented, and may reproduce the invention in the embodiments presented, and in other variants encompassed in the scope of the appended claims.

The invention claimed is:

1. A method of generating a multilayered-lining garment, comprising:
    providing a first layer, a second layer, a third layer, a fourth layer, and a fifth layer;
    cutting the first layer, the second layer, and the third layer to have a size equal to one another;
    sewing the third layer and the fourth layer together at a position that is approximately 1 to 3 cm from side edges of the third layer;
    sewing the first layer, the second layer and the third layer together at first and third end edges thereof;
    sewing the fifth layer together with the first layer, the second layer, and the third layer at side edges thereof that define openings of lining-legs by using fabric tape or sewing; and
    joining the first layer, the second layer, the third layer and the fifth layer by sewing with elastics, laces, or other finishings.

2. The method of claim 1, wherein the sewing is performed using needles from size 60 to size 90.

3. The method of claim 1, wherein the sewing is performed using polyester thread 120 to 160 or polyester thread with antimicrobial and anti-leak treatment.

4. The method of claim 1, wherein the fifth layer includes a finishing material comprising one or more of cotton, modal, bamboo, viscose, polyester, microfiber, nylon, including combinations with elastane, lycra, and spandex.

5. The method of claim 1, wherein the first layer includes a natural or synthetic material including one or more of cotton, polyester, bamboo, viscose, tinsel, modal, and nylon.

6. The method of claim 1, wherein the first layer includes a natural or synthetic material that includes a branched, woven fabric, fleece, terrycloth, or microfiber structure.

7. The method of claim 6, wherein the third layer is knitted or woven, and optionally includes 51% of modal, viscose, bamboo, carbon, or cotton having 90 to 300 gsm2.

8. The method of claim 6, wherein the fourth layer includes at least 90% either of polyester or microfiber having 100 to 300 gsm2.

9. The method of claim 1, wherein the first layer includes a natural or synthetic material that is between 60 and 350 g/m2 by weight.

10. The method of claim 1, wherein the first layer includes breathable thermoplastic polyurethane having thickness in a range from approximately 0.015 to approximately 0.020 mm that is not treated with a chemical product.

11. The method of claim 1, wherein the multilayered-lining garment further includes a sixth layer, and the sixth layer or the third layer is chemically treated with an antimicrobial product.

12. The method of claim 1, further comprising:
a sixth layer;
treating one or more of the third layer, the fourth layer and the sixth layer with an antimicrobial product; and
joining the third layer, the fourth layer, and the sixth layer by a U-shaped seam.

13. The method of claim 1, further comprising:
using the multilayered-lining garment to generate a garment having a form of a bra.

14. The method of claim 1, further comprising:
sewing the fifth layer on an inner garment layer.

15. The method of claim 1, further comprising:
sewing the first layer using an additional finishing stitch on a gusset.

16. The method of claim 11, wherein the antimicrobial product contains zinc.

17. The method of claim 1, wherein the fourth layer is approximately 0.1 to 0.3 cm smaller in length than a length of the first layer, the second layer, and the third layer.

18. The method of claim 1 wherein the first layer, the second layer and the fourth layer are disposed between the third layer and the fifth layer;
the first layer is an antimicrobial layer, the second layer is a waterproofing layer, and the fourth layer is an absorbent layer;
the first layer is disposed between the second layer and the fifth layer;
the second layer is disposed between the first layer and the fourth layer;
the fourth layer is disposed between the second layer and the third layer.

19. The method of claim 1, wherein sewing the third layer and the fourth layer together comprises using chain stitch (ISO 101), zig-zag lockstitch (ISO304), or three-thread overedge stitch (ISO 401); and
sewing the fifth layer together with the first layer, the second layer, and the third layer at side edges thereof that define openings of lining-legs by using fabric tape or sewing comprises using blind stitch, three-thread overedge stitch (ISO 504), zig-zag lockstitch (ISO 304) or bottom cover stitch (ISO 406).

* * * * *